United States Patent
Mollstam et al.

(10) Patent No.: US 6,872,565 B2
(45) Date of Patent: Mar. 29, 2005

(54) **PRODUCT CONTAINING *LACTOBACILLUS REUTERI* STRAIN ATTC PTA-4965 OR PTA-4964 FOR INHIBITING BACTERIA CAUSING DENTAL CARIES**

(75) Inventors: Bo Mollstam, Lerum (SE); Eamonn Connolly, Lidingo (SE)

(73) Assignee: Biogaia AB, Stockholm (SE)

( * ) Notice: Subject to any disclaimer, the term of this patent is extended or adjusted under 35 U.S.C. 154(b) by 88 days.

(21) Appl. No.: 10/353,407

(22) Filed: Jan. 29, 2003

(65) Prior Publication Data

US 2004/0146493 A1 Jul. 29, 2004

(51) Int. Cl.[7] .............................. C12N 1/00; C12N 1/20
(52) U.S. Cl. ..................... 435/252.9; 435/853; 424/439
(58) Field of Search .............................. 435/252.9, 853, 435/822; 424/439, 93.45

(56) References Cited

U.S. PATENT DOCUMENTS

| | | |
|---|---|---|
| 5,413,960 A | 5/1995 | Dobrogosz |
| 5,439,678 A | 8/1995 | Dobrogosz |
| 5,800,813 A | 9/1998 | Casas |
| 5,837,238 A | 11/1998 | Casas |
| 5,849,289 A | 12/1998 | Dobrogosz |
| 6,036,952 A | 3/2000 | Oh |
| 6,100,388 A * | 8/2000 | Casas et al. ................ 536/23.5 |
| 6,103,227 A | 8/2000 | Wolf |
| 6,461,607 B1 * | 10/2002 | Farmer ..................... 424/93.45 |

FOREIGN PATENT DOCUMENTS

| | | |
|---|---|---|
| WO | PCT/FR92/00126 | 9/1992 |
| WO | PCT/EP00/07919 | 3/2001 |

OTHER PUBLICATIONS

Babaahmady, Efficiency of *Lactobacillus rhanmosus* GG against dental caries, Yogurts, Jun. 2002.
Fitzgerald, Cariogenicity of human oral *lactobacilli* in hamsters, J. Dent. Res. 59(5):832–7, 1980.
Jacques, Characterization of two strains of cariogenic *lactobacilli*, J. Gen.Microbiol. 118:283, 1980.
Nase, Effect of long–term consumption of a probiotic bacterium, Lac . . . , Caries Res. 35:412, 2001.

* cited by examiner

Primary Examiner—David M. Naff
Assistant Examiner—Deborah K. Ware
(74) Attorney, Agent, or Firm—Lynn E. Barber

(57) ABSTRACT

Strains of *Lactobacillus* that have been selected for their capability of reducing the number of *Streptococcus mutans* in the mouth of mammals through inhibiting activity in combination with good binding to the oral mucins and dental plaque, Administering the strains in a product such as food, reduces and treats dental caries. Preferred strains are *Lactobacillus reuteri* strain ATTC PTA-4965 or *Lactobacillus reuteri* strain ATTC PTA-4964.

7 Claims, No Drawings

PRODUCT CONTAINING *LACTOBACILLUS REUTERI* STRAIN ATTC PTA-4965 OR PTA-4964 FOR INHIBITING BACTERIA CAUSING DENTAL CARIES

BACKGROUND OF THE INVENTION

1. Field of the Invention

This invention relates to use of a method for screening nonpathogenic anti-cariogenic strains, and products and methods using such strains for treatment and prophylaxis of dental caries caused by oral bacteria such as *Streptococcus mutans*, and other caries-causing pathogens.

2. Description of the Related Art

The oral cavity of humans and other mammals contains many different species of bacteria, including a number of different species of *Lactobacillus*. Caries is a disease caused by bacteria. In 1890, Miller in "Chemico-Parasitic Theory" presented the hypothesis that caries is caused by oral bacteria producing acids from digestive carbohydrates, which dissolve the hydroxyhepatite of the teeth. It was later confirmed in gnotobiotic rats, for example, that normal oral bacterial flora, are involved, primarily of the *mutans streptococci* group, and also that the lactobacilli group is involved. These "acidogenic" species resident in the oral cavity are associated with the presence and onset of dental caries (Locsche W J, Microbiolog Rev.,1986:50:353–380). There are seven bacterial species within the group *mutans streptococci,* with *Streptococci mutans* (serotype c,e,f) being found in 90% of all human isolates (Linder L., Oral Mikrobiologi 1996, ISBN 91-7205-037-3). There is abundant evidence that the initiation of caries requires a relatively high proportion of *S. mutans* within dental plaque. These bacteria adhere well to the tooth surface, produce higher amounts of acid from sugars than other bacterial types, can survive better than other bacteria in an acid environment, and produce extracellular polysaccharides from sucrose. When the proportion of *S. mutans* in plaque is high (in the range of 2–10%), a patient is at high risk for caries. When the proportion is low (less than 0.1%), the patient is at low risk. Because they are more acid tolerant than other bacteria, acid conditions within plaque favor the survival and reproduction of *mutans streptococci.* Two other types of bacteria are also associated with the progression of caries through dentin. These are several species of *Lactobacillus,* and *Actinomyces viscosus.* These bacteria are also highly acidogenic and survive well in acid conditions. The involvement of *Lactobacillus* in dental caries has been established (Smith et al., Microbios 105: 77–85, 2001). In fact, estimation of the lactobacillus counts in saliva, in addition to the estimation of *mutans streptococci* counts, using different selective media or other techniques, has been used for many years as a "caries test" and to attempt to identify groups at high risk for caries. Thus, *Lactobacillus* strains, some isolated from human dental plaque, may be highly cariogenic (Fitzgerald et al., J. Dent. Res. 60: 919–926, 1981.

For a bacteria to be a primary pathogen in the formation of dental caries it is required that it have a combination of several of the required characteristics (Linder, 1996): ability to adhere and colonize on the teeth surface; ability to accumulate in large numbers on a limited surface of the teeth; ability to quickly produce acid from carbohydrates found in foods; and ability to continue acid production even under low pH in the dental plaque.

Dietary sucrose changes both the thickness and the chemical nature of plaque. Mutans streptococci and some other plaque bacteria use the monosaccharide components (glucose and fructose) and the energy of the disaccharide bond of sucrose to assemble extracellular polysaccharides. These increase the thickness of plaque substantially, and also change the chemical nature of its extracellular space from liquid to gel. The gel limits movement of some ions. Thick gel-plaque allows the development of an acid environment against the tooth surface, protected from salivary buffering. Plaque which has not had contact with sucrose is both thinner and better buffered. A diet with a high proportion of sucrose therefore increases caries risk. Thicker plaque occurs in pits and fissures and, in patients with poor oral hygiene, near the gingival margin.

Given this concept of the nature of the disease, it is clear that prevention and treatment of dental caries requires hindering the effects of *S. mutans,* for example, through dietary change as means of reducing the substrate for the bacteria, to reinforce the surface structure of the teeth or reduction of the number of *S. mutans* bacteria. Thus, treatments that have been tried include: efforts at changing the microflora, using agents such as topical chlorhexidine and topical fluoride; reducing the amount of dietary sucrose, by dietary change and substitution for sweeteners more difficult to metabolize by *S. mutans,* such as Sorbitol, Aspartan, Xylitol; decreasing the frequency of eating, by dietary choice; adding fluoride, particularly through daily application during tooth brushing; and increasing salivary flow, using mechanical stimulation during vigorous chewing to enhance flow, by changing drugs which reduce flow, or by using drugs to enhance flow. Different approaches has been evaluated for preventing dental caries, for example, one composition uses a lytic enzyme produced by a bacteriophage specific for *Streptococcus mutans* (U.S. Pat. No. 6,399, 098 of Fischetti et al.). Also, a strain of *Lactobacillus zeae* has been modified through genetic engineering to produce an antibody on its surface to neutralize the detrimental streptococcal bacteria, (Hammarstrom L., July 2002 issue of Nature Biotechnology), however this approach with genetically modified organisms faces an unknown safety approval situation.

In addition, one strain of *Lactobacillus rhamnosus* (strain GG) has been promoted as a probiotic method of reducing *Streptococcus sabrinus* and *mutans streptococci* generally (Nase et al., Caries Res. 35: 412–420, 2001). Further work showed that use of this strain as a starter in fermenting milk did not influence the titer of antibodies against human cariogenic bacteria that were present in the milk (Wei et al., Oral Microbio. & Immunol. 17: 9–15, 2002. *L. rhamnosus* GG differs from *L. reuteri* in many ways, including fermentation characteristics and isolation source. Other microorganisms that have been found to have inhibitory activity against the formation of dental plaque include *Enterococcus, Lactobacillus acidophilus* V20, and *Lactobacillus lactis* 1370 (Oh, U.S. Pat. No. 6,036,952). In order to inhibit *S. mutans,* other work has been done using so called "competitive exclusion" concepts. For example, *L. reuteri* strain ATCC 55730 has been shown to inhibit *S.mutans* (Nikawa H. et al, News release by Hiroshima University Jul. 11, 2002). A tablet product which is on the market in Japan called LS1, containing a strain of *Lactobacillus salivarius* (LS 1) (by Frente Ltd. Japan) is claimed to inhibit *S.mutans.*

Strains of a wide variety of *Lactobacillus* species, including *Lactobacillus reuteri,* have been used in probiotic formulations. *Lactobacillus reuteri* is one of the naturally occurring inhabitants of the gastrointestinal tract of animals, and is routinely found in the intestines, and occasionally in the birth channel, breast milk and mouth of healthy animals, including humans. It is known to have antibacterial activity. See, for example, U.S. Pat. Nos. 5,439,678, 5,458,875, 5,534,253, 5,837,238, and 5,849,289. When L. reuteri cells are grown under anaerobic conditions in the presence of glycerol, they produce the antimicrobial substance known as reuterin (β-hydroxy-propionaldehyde). Other antimicrobial substances beside the traditional organic acids have also been reported such as "Reutericyclin" (Höltzel, A. et al. Angewandte Chemie International Edition 39, 2766–2768, 2000) and "PCA (pyroglutamic acid)" (Yang, Z. Dissertation, Univ. of Helsinki, March 2000). Lactobacilli, including L. reuteri, are also well known to have the ability to inhibit other organisms such as S. mutans through local competition of nutrients and other metabolic interactions. Immunomodulating and anti-inflammatory activity has also been associated with L. reuteri. Mucin binding proteins of L.reuteri have been isolated and described. See, for example, U.S. Pat. No. 6,100,388.

Lactobacillus strains have been reported to adhere to various cell lines and host mucus. This has been speculated to be important for probiotic activity and is derived from the concept of virulence factors in pathogenic bacteria, where vast arrays of such interactions have been discovered during the last decades (Klemm, P. and Schembri, M. A. (2000) Bacterial adhesins: function and structure. Int. J. Med. Microbiol. 290, 27–35.)

While the possibility of effective antibacterial activity by L. reuteri is known, and certain binding characteristics of L.reuteri such as mucin binding are known, and S.mutans inhibiting effects of L.reuteri strain ATCC 55730 and Lactobacillus GG ATCC 53103 are also known, it was not previously known that substantial differences existed between lactobacilli strains in their ability to reduce the number of Streptococci mutans in the oral cavity and thereby caries, as a consequence of both inhibiting effect and binding activity, nor that such strains could be selected.

It is therefore an object of the invention to provide better strains of Lactobacillus which have been selected for their capability of reduce the number of S. mutans in the mouth through antimicrobial activity in combination with good binding to the oral mucins and dental plaque and thereby prevent, reduce or treat dental caries. It is a further object of the invention to provide products containing said strains, including agents for prophylaxis or treatment of caries associated with S.mutans for administration to humans.

Other objects and advantages will be more fully apparent from the following disclosure and appended claims.

SUMMARY OF THE INVENTION

The invention herein comprises strains of Lactobacillus that have been selected for their capability of reducing the number of Streptococcus mutans in the mouth of mammals through inhibiting activity in combination with good binding to the oral mucins and dental plaque, thereby preventing, reducing or treating dental caries, products derived from said strains, including agents for treatment or prophylaxis of caries for administration to humans, and a method for producing these products.

Other objects and features of the inventions will be more fully apparent from the following disclosure and appended claims.

DETAILED DESCRIPTION OF THE INVENTION AND PREFERRED EMBODIMENTS THEREOF

The present invention provides a product, for inhibiting the growth and activity of dental caries bacteria, comprising cells of at least one selected strain of Lactobacillus with both good antimicrobial activity against Streptococci mutans combined with good binding to the oral mucins and dental plaque and thereby prevent, reduce or treat dental caries. Such strains include L. reuteri CF2-7F (ATTC No. PTA-4965. deposited on Jan. 28, 2003, and available to the public under the Budapest Treaty) and L. reuteri MF2-3 (ATTC No. PTA-4964 deposited on Jan. 28, 2003, and available to the public under the Budapest Treaty). These strains are deposited at the American Type Culture Collection. P.O. Box 1549. Manassas. Va.

In addition to their ability to reduce the number of Streptococci mutans in the oral cavity, the other criterion for Lactobacillus strain selection in this invention is the ability of the strain to adhere to the host mucins. Indeed, it has been shown that lactobacilli do adhere to mucosal surfaces and components thereof. Working with adhesion of lactobacilli to mucus revealed that many strains apparently lack the ability to bind mucus material in vitro. Since many of these non-binders were isolated from mucosal surfaces, it could be assumed that the environment of growth could affect the adhesion properties of the bacteria.

In the selection method used herein, the adhesion characteristics have been examined by partly mimicking the intestinal environment by including mucin in the bacterial growth medium. Thus, as discussed in the Examples, the method of selection of the invention comprises: 1) evaluation of the inhibiting effect of S. mutans by Lactobacillus strains; and 2) evaluation of mucin binding effect by Lactobacillus.

The product of the invention can be any product for placement in the mouth as a preventative or treatment for dental caries, or for nutritional or breath purpose, such as food products, dental treatment products such as mouthwashes or other specified health product, chewing gum, and the like. Food products lending themselves particularly to use in the invention include milk-containing products such as yogurt, and also juices, drinks and the like. Preferred food products to use in the invention are yogurt, jelly, pudding, chewing gum, candy, chocolate, biscuits, cookies, cheese, juice and tea. The dental treatment products that may be used in the invention include toothpastes, liquid tooth cleansers, mouthwashes, anti-halitosis products, and the like.

The concentration of selected Lactobacillus cells needed for effectiveness of a product of the invention depends on the type of food and the amount of food to be ingested (or the time of use in the mouth of a non-food dental treatment product), but it is usually preferable to have about $10^6$–$10^7$ CFU (colony-forming units) or more per gram of a product. Amounts up to about $10^{10}$-$10^{11}$ CFU are possible and can be used to increase efficacy without adversely affecting the product's organoleptic characteristics (its flavor or smell). When the product is yogurt or other lactic acid fermentation product, the lactic acid fermentation strain(s) used to produce the product would preferably be standard cultures for this particular purpose, and the anti-cariogenic bacteria of the invention may be added either before or after the fermentation of the product at a level of about $10^6$–$10^7$ CFU per ml of yogurt or more as discussed above.

Preferably the product of the invention does not contain other antibacterial components, at least none that inhibit or kill selected Lactobacillus strain(s) or interfere with its anti-cariogenic activity.

The strain(s) of Lactobacillus can be an additive mixed into the ingredients or kneaded into or coated on the product by means known in the art for formulation of products of that type. If preparation of the selected food or other product of the invention requires a heating step, the *Lactobacillus* strain(s) should be added after the heating. Once the selected *Lactobacillus* cells are in the product, it is preferred not to heat the product to 60–70 degrees C. or above for a longer period of time.

The features of the present invention will be more clearly understood by reference to the following examples, which are not to be construed as limiting the invention.

EXAMPLE 1

Method of Selection of Strains

The selection of the *Lactobacillus* strains to be used according to this invention can be done in the following two step manner:

a) Evaluation of Inhibiting Effect of *S. mutans* by *Lactobacillus* Strains

An example of a strain to use to measure the inhibitory effect is *Streptococcus mutans*, ATCC25175 (available from The American Type Culture Collection, Manassas, Va., USA). The isolate is grown in trypticase soy broth (Difco, Detroit, USA) supplemented with 0.5% yeast extract (Difco) (TSBY). The cells are harvested during the exponential growth phase by centrifugation at 1000×g, washed twice with PBS and resuspended in the same buffer. The cell suspensions are subjected to a low-intensity ultrasonic device to disperse bacterial aggregates.

The test *Lactobacillus* strain is grown in brain-heart infusion broth (Difco), harvested during the exponential growth phase by centrifugation at 1000×g, washed twice with phosphate buffered saline (PBS; pH 6.8) and re-suspended in the same buffer.

The optical densities of the bacterial suspensions are measured in a 1.0 ml cuvette with a 1 cm light path, and the suspensions is adjusted to a final concentration of $1.0 \times 10^8$ CFU (colony forming unit)/ml.

The inhibitory assay is conducted as follows, the suspension of *S. mutans* and the suspension of *Lactobacillus* are mixed in the ratios of 100-0, 75-25, 50-50 and 25-75 in sterile centrifugation tube (total volume 100 µl), added the BHI broth up to 10 ml, vortex mixed for ten seconds and incubated for 90 min at 37° C. with gentle shaking. As a control, the suspension of *S. mutans* is mixed with an equal volume of PBS in the control tubes (free of *Lactobacillus*). Afterwards each suspension is washed by centrifugation at 1000×g, washed twice with PBS, and plated on MS agar to determine the CFU count of *S. mutans*. The % survival of *S. mutans* is obtained from following formula.

$$\% \text{ survival of } S. \text{ mutans} = \frac{\text{CFU of } S. \text{ mutans incubated with } Lactobacillus}{\text{CFU of } S. \text{ mutans incubated with PBS}} \times 100$$

The assay should be carried out with minimum triplicate samples. All the numerical data obtained should be statistically analyzed.

b) Evaluation of Mucin Binding Effect by *Lactobacillus*

Mucine from porcine stomach (Sigma, St. Louis, Mo., USA) is suspended in carbonate buffer at pH 9.7 at a concentration of 0.1 mg/ml 200 µl of the solution is pipetted into microtiter wells and is left for coating at 37° C. for approximately 3 hours. The wells are blocked by the addition of 200 µl PBS 1% Tween20 at room temperature for 1 hour and washed 3 times with PBS 0.5% Tween20 (PBST). The *Lactobacillus* evaluation strains are grown overnight at 37° C. in MRS broth supplemented with 0.01% pig gastric mucin (Sigma, M1778) to mimic the growth conditions in vivo, then washed and re-suspended in PBST. Optical density (OD) of the bacterial cells is measured at 600 nm in a Beckman DU650 spectrophotometer and adjusted to OD 0.5. 100 µl bacterial suspension is added to each well and incubated overnight at 4° C. The wells are washed with PBST, and binding is examined with an inverted microscope. The buffer is poured off and, after the wells had dried, OD405 measured in an ELISA plate reader. The results of the binding is scored on a scale from 0 to 3, where 0 is no binding and 3 is strong binding to the mucin.

The *Lactobacillus* strains showing best results in both inhibiting of *S.mutans* as well as binding to mucin, according to the assays are selected.

EXAMPLE 2

Selection of Strains

1. *L. reuteri* SD2112 (ATCC 55730)
2. *L. reuteri* DSM 20016 (DSM 20016)
3. *L. reuteri* MM2-3 (ATCC PTA-4659)
4. *L. reuteri* CF2-7F (ATTC PTA-4965)
5. *L. reuteri* MF2-3 (ATTC PTA-4964)
6. *L. reuteri* MF14-C (Culture collection of Biogaia AB, Raleigh N.C., USA)
7. *L. reuteri* MF52-1F (Culture collection of Biogaia AB, Raleigh N.C., USA)
8. *L. salivarius* LS1 (isolated from the LS1 tablet by Frente Ltd. Japan)
9. *L. rhamnosus* GG (ATCC 53103)

In this study the above listed *Lactobacillus* strains are chosen to be evaluated using the selection criteria of inhibition of *S. mutans* and adhesion to mucin according to the invention. The methods set forth in Example 1 are used. The strains that were selected to be the most suitable strains are based on the combination of the *S. mutans* inhibiting effect and the adhesion of cells of the *Lactobacillus* strain to mucin.

TABLE 1

Inhibition of *S. mutans* of *Lactobacillus* strains as well as adhesion score to mucin according to the described assays. (0 = no binding, 3 = high binding, S = selected)

| CFU/g survival | CFU/g survival | CFU/g survival | CFU/g survival | Mucin binding |
| --- | --- | --- | --- | --- |

| Strain | S. mutans ratio 10:1 | S. mutans ratio 3:1 | S. mutans ratio 1:1 | S. mutans ratio 1:3 | score (0–3) | Selection |
|---|---|---|---|---|---|---|
| L. reuteri SD2112 | 2.0E+08 | 8.0E+07 | 6.0E+07 | 9.0E+06 | 2 | — |
| L. reuteri DSM 20016 | 1.0E+08 | 2.0E+07 | 7.0E+06 | 3.0E+05 | 3 | S |
| L. reuteri MM2-3 | 1.0E+08 | 7.0E+07 | 5.0E+07 | 9.0E+06 | 3 | — |
| L. reuteri CF2-7F | 1.0E+08 | 1.0E+07 | 7.0E+05 | 9.0E+04 | 3 | S |
| L. reuteri MF2-3 | 2.0E+08 | 2.0E+07 | 4.0E+06 | 1.0E+05 | 2 | S |
| L. reuteri MF14-C | 9.0E+07 | 8.0E+07 | 7.0E+07 | 3.0E+07 | 1 | — |
| L. reuteri MF52-1F | 1.0E+08 | 8.0E+07 | 7.0E+07 | 3.0E+07 | 1 | — |
| L. salivarius LS1 | 1.0E+08 | 8.0E+08 | 7.0E+09 | 3.0E+09 | 0–1 | — |
| L. rhamnosus GG | 2.0E+08 | 8.0E+07 | 7.0E+07 | 3.0E+07 | 0–1 | — |

EXAMPLE 3

Confirmation of Efficacy of Selected Lactobacillus Strains

The effects of milk fermented with added evaluated Lactobacillus strains (test Yogurt) according to the list of Example 2, and placebo fermented milk (Placebo Yogurt) on oral carriage of mutans streptococci is studied. The test yogurts are:

Test yogurt 1.with L. reuteri SD2112
Test yogurt 2 . . . with L. reuteri DSM 20016
Test yogurt 3 . . . with L. reuteri MM2-3
Test yogurt 4 . . . with L. reuteri CF2-7F
Test yogurt 5 . . . with L. reuteri MF2-3
Test yogurt 6 . . . with L. reuteri MF14-C
Test yogurt 7 . . . with L. reuteri MF52-1F
Test yogurt 8 . . . with L. salivarius LS1
Test yogurt 9 . . . with L. rhamnosus GG
Test yogurt 10 Placebo, see below 200 healthy female subjects (age; 20 plus or minus 2 year) are divided into 10 groups. All subjects shall not have any active caries lesions, symptom of either gingivitis or periodontal disease. Subjects in the first group eat a cup (95 g) of Placebo Yogurt at lunch time (12:00–1300) every day, for two weeks and then eat a cup of Test Yogurt no. 1, at lunch time for another two weeks. Subjects in the second group eat a cup (95 g) of Placebo Yogurt at lunch time (12:00–1300) every day, for two weeks and then eat a cup of Test Yogurt no. 2, at lunch time a day, for another two weeks, and so on for all 9 first groups. Test group no. 10 eat Placebo Yogurt for both periods. Before and after the eating of each kind of yogurt, the levels of oral carriage of mutans streptococci is determined, as follows. Approximately 5 ml of unstimulated whole saliva is collected in a container on ice at 15:00–16:00. Then the oral carriage of mutans streptococci is determined by conventional viable counts. Placebo Yogurt are comprised of L. bulgaris and S. thermophilus, which are widely employed in fermented milk products, the placebo yogurt are heated to 80° C. for 10 min to kill microorganisms and prepared as Test yogurt no 10. Both the subjects and investigators are unaware of which yogurt contained which test organism throughout the study. The use of other products containing Lactobacillus or other pharmaceutical lactic acid bacteria is forbidden for one week prior to and throughout the intervention. The data is analyzed statistically.

TABLE 2

Result from In vivo inhibition of S. mutans by lactobacilli strains, data in log (CFU of oral streptococci)

| Yogurt and Strain | Start | After Placebo | After Test |
|---|---|---|---|
| Test yogurt 1: L. reuteri SD2112 | 5.0E+05 | 6.0E+05 | 1.0E+05 |
| Test yogurt 2: L. reuteri DSM 20016 | 3.0E+05 | 2.0E+05 | 4.0E+04 |
| Test yogurt 3: L. reuteri MM2-3 | 2.0E+05 | 4.0E+05 | 1.0E+05 |
| Test yogurt 4: L. reuteri CF2-7F | 1.0E+05 | 7.0E+05 | 9.0E+02 |
| Test yogurt 5: L. reuteri MF2-3 | 9.0E+04 | 7.0E+05 | 2.0E+03 |
| Test yogurt 6: L. reuteri MF14-C | 1.0E+03 | 4.0E+05 | 1.0E+05 |
| Test yogurt 7: L. reuteri MF52-1F | 3.0E+04 | 7.0E+05 | 2.0E+05 |
| Test yogurt 8: L. salivarius LS1 | 4.0E+05 | 7.0E+05 | 1.0E+06 |
| Test yogurt 9: L. rhamnosus GG | 8.0E+04 | 4.0E+05 | 1.0E+05 |
| Test yogurt 10: PLACEBO | 7.0E+05 | 9.0E+05 | 1.0E+06 |

EXAMPLE 4

Manufacturing of Products Containing Selected Strain

In this example, L. reuteri CF2-7F (ATTC PTA-4965), was selected, using the methods above for S. mutans inhibition and mucin binding, in order to add the strain to a standard yogurt. The L. reuteri strain was grown and lyophilized, using standard methods for growing Lactobacillus in the dairy industry. This culture was then added to previously fermented milk, using traditional yogurt cultures, at a level of $10^7$ CFU/gram of yogurt, and the yogurt was used by humans as a way to prevent caries.

While certain representative embodiments have been set forth herein, those skilled in the art will readily appreciate that modifications can be made without departing from the spirit or scope of the invention.

What is claimed is:

1. A product for inhibiting growth of dental caries bacteria, comprising cells of at least one strain of Lactoba-

*cillus reuteri* selected from the group consisting of *Lactobacillus reuteri* strain ATTC PTA-4965 and *Lactobacillus reuter*, strain ATTC PTA-4964, said strains having inhibitory activity against cariogenic bacteria in combination with good binding to oral mucins.

2. The product according to claim 1 wherein the product is a food product.

3. The product according to claim 2, wherein the food product is selected from the group consisting of yogurt, jelly, pudding, chewing gum, candy, chocolate, biscuit, cookie, cheese, juice and tea.

4. The product according to claim 2, wherein the food product is a milk-containing product.

5. The product according to claim 4, wherein the food product is yogurt.

6. The product according to claim 1, wherein the product is a dental treatment product.

7. The product according to claim 6, wherein the product is a mouthwash.

* * * * *